US005570193A

United States Patent [19]
Landa et al.

[11] Patent Number: 5,570,193
[45] Date of Patent: Oct. 29, 1996

[54] CONCENTRATION DETECTOR FOR COLORED TONER

[75] Inventors: Benzion Landa, Edmonton, Canada; Yehuda Niv, Rehovot, Israel; Michael Plotkin, Kibbutz Einat, Israel; Peter Forgacs, Kiryat Gat, Israel

[73] Assignee: Indigo N.V., SM Veldhoven, Netherlands

[21] Appl. No.: 360,681

[22] PCT Filed: Jul. 2, 1992

[86] PCT No.: PCT/NL92/00117

§ 371 Date: Feb. 27, 1995

§ 102(e) Date: Feb. 27, 1995

[87] PCT Pub. No.: WO94/01809

PCT Pub. Date: Jan. 20, 1994

[51] Int. Cl.⁶ .................................... G01N 21/59
[52] U.S. Cl. .................. 356/442; 356/436; 356/440
[58] Field of Search .................... 356/436, 440, 356/442

[56] References Cited

U.S. PATENT DOCUMENTS 3,233,781  2/1966  Grubbs.
4,416,538  11/1983  Mueller et al. ............. 355/67
4,579,253  4/1986  Shenier.
4,660,152  4/1987  Downing et al. ............ 364/509
4,981,362  1/1991  deJong et al. ............. 356/442

FOREIGN PATENT DOCUMENTS 1148943  6/1989  Japan.
1387696  3/1975  United Kingdom.

OTHER PUBLICATIONS

English Language Abstract of JP-62-99774.
English Language Abstract of JP-62-099775.
English Language Abstract of JP-62-140061.

Primary Examiner—Richard A. Rosenberger
Attorney, Agent, or Firm—Greenblum & Bernstein P.L.C.

[57] ABSTRACT

Apparatus for detecting concentrations of colored toner particles in the presence of black or other absorbing toner particles including a light source, a light detector having a field of view of less than about ±10 degrees and preferably less than ±5 degrees, apparatus for supplying a dispersion of colored toner particles optionally containing undesirable contamination by black toner particles between the light source and the detector and computing circuitry operative for determining the concentration of the colored toner particles utilizing output from the light detector.

37 Claims, 2 Drawing Sheets

CONCENTRATION DETECTOR FOR COLORED TONER

FIELD OF THE INVENTION

The present invention relates to the field of concentration detection and more particularly to the detection of toner concentration in color liquid developer compositions especially in the presence of contaminants.

BACKGROUND OF THE INVENTION

In liquid developer systems the liquid developer is generally comprised of a carrier liquid and toner particles in a generally constant ratio. During imaging operations the concentration of toner particles is reduced and concentrated toner is added to return the concentration to its desired value.

It is important that the concentration of particles should be kept within a given range in order to realize consistent copy quality. This requirement is especially important in color printers or copiers, where the quality of the images is especially dependent on the color balance and on its stability.

In general, concentration of toner particles in liquid developers is determined by measuring the attenuation of light passing through a given path filled with the liquid developer. Since the particles absorb and scatter light, the attenuation of the light is related to the concentration of the particles.

U.S. Pat. No. 4,579,253 describes a system in which the beam of light is split into two components only one of which is attenuated by the liquid developer. The concentration is determined from the ratio of the attenuated and unattenuated beams.

Such systems work fairly well in single color systems or in multicolor systems in which there is no cross contamination between the colors. In general, the most troublesome cross-contamination is black toner particles in a relatively low attenuation color such as yellow. Since black has an attenuation several times that of yellow, visually negligible black contamination can effect the determination of the color concentration in a way which seriously disturbs the color balance of the system.

Japanese Patent Publication Kokai 1-148943 describes a system in which the attenuation of beams of light having two different colors are sequentially measured. Using these attenuation values, the publication describes a method for determining the concentration of both the black and the color particles.

Generally speaking, measurement of attenuation caused by toner particles is most effective when a large cross-section is viewed, since this increases the signal level for the brightness of light source. This preferred operation requires a detector with a wide field of view.

SUMMARY OF THE INVENTION

The present invention is based on an analysis of the different factors which are operative in the attenuation of light by toner particles dispersed in a carrier liquid.

The two main factors are the absorption of light and the scatter of light by the particles. In general, for black toner particles, the effect of scatter is very small compared to the effect of absorption. On the other hand, for colored toner particles, especially for yellow, the effect of scatter is much greater than that of absorption.

In a preferred embodiment of the invention, the relative sensitivity to scattering measurements is improved by reducing the angle of view of a detector which detects light passing through the dispersion.

When a wide field of view is used much of the light which reaches the detector may be caused by multiple scattering. When black or other mainly absorbing toners are measured this effect is unimportant. However, when colored toners are present this multiple scattering greatly reduces the sensitivity of the system.

For maximum sensitivity, light which is scattered by a colored toner particle should be removed from the system and should not reach the detector. However, when the angle of view of the detector is wide, light which is scattered is generally rescattered and a portion of the rescattered light reaches the detector. The larger the angle the greater the problem.

In a preferred embodiment of the invention the angle of view of the detector is limited to less than ±10 degrees, preferably less than ±5 degrees. At these angles, the relative sensitivity to color over black is increased. The only lower limit on the angle is the brightness of the source, since the total signal received by the detector decreases with decreasing angle.

There is therefore provided in a preferred embodiment of the invention apparatus for detecting concentrations of colored toner particles in the presence of black or other absorbing toner particles including:

a light source;

a light detector having a field of view of less than about ±10 degrees, preferably less than about ±5 degrees;

means for supplying a dispersion of colored toner particles optionally containing undesirable contamination by black toner particles between the light source and the detector; and computing circuitry operative for determining the concentration of the colored toner particles utilizing output from the light detector.

In a preferred embodiment of the invention the light source includes a lamp and a collimating lens. Preferably, the light detector includes a focusing lens.

In a preferred embodiments of the invention the field of view is limited by the size of the detector, the size of the focusing lens and/or an iris.

Preferably, the lamp is a laser diode or other laser source. An alternative preferred source is a LED or a bright lamp.

In a preferred embodiment of the invention the amount of black contamination can be determined. In this embodiment there is further provided a second light detector having a large field of view and computing circuitry operative for determining the concentration of the black toner particles utilizing output from the second light detector.

There is further provided, in accordance with a preferred embodiment of the invention a method for detecting the concentration of colored toner particles in a dispersion undesirably contaminated by black toner particles, the method including the steps of:

providing a quantity of the dispersion of colored toner particles optionally contaminated with black toner particles;

illuminating the dispersion;

detecting an amount of light passed through the dispersion with a viewing angle of less than ±10 degrees; and determining the concentration of the colored toner particles utilizing the detected amount of light.

BRIEF DESCRIPTION OF THE DRAWINGS

The invention will be better understood from the following detailed description of the preferred embodiments of the invention in conjunction with the following drawings in which.

DETAILED DESCRIPTION OF PREFERRED EMBODIMENTS

Figure 1:
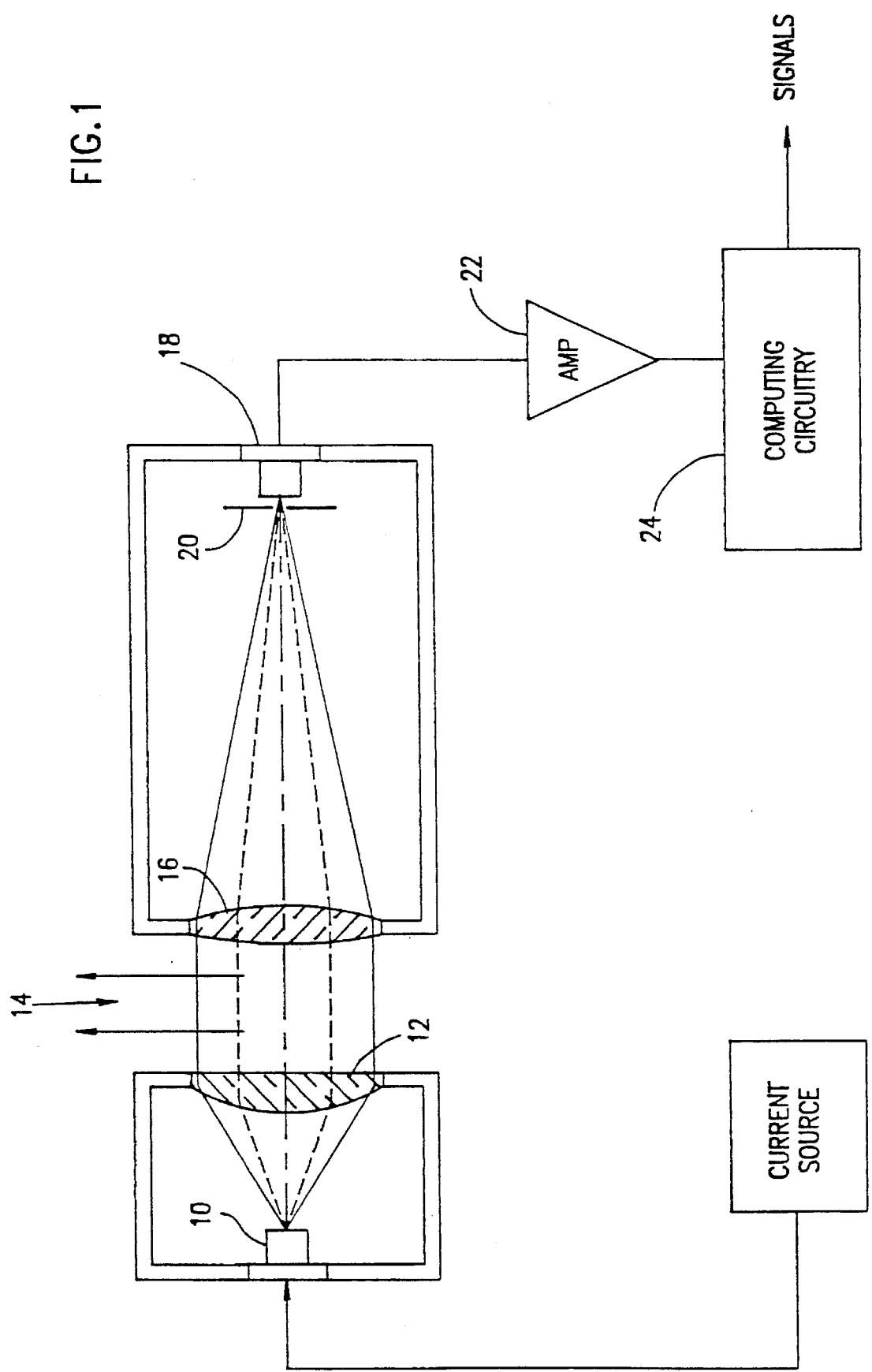
FIG. 1 is a schematic illustration of a concentration detector constructed and operative in accordance with an embodiment of the present invention.

Reference is now made to FIG. 1 which illustrates a concentration detector constructed and operative in accordance with a preferred embodiment of the present invention.

The concentration detector typically comprises a source of light 10 which may be a lamp or a laser diode, a collimating lens 12 which collimates the light from lamp 10 and passes it through a dispersion 14 of toner particles in carrier liquid. Preferably, an iris 11 is included to improve the collimation, i.e., to reduce the angular extent of the light. Preferably, dispersion 14 flows through channel between lens 12 and a focusing lens 16. Focusing lens 16 focuses the light which passes through dispersion 14 onto a detector element 18, for example a photodiode or a photoresistor. The system optionally includes an iris 20 at the focus of the light for limiting the field of view seen by detector element 18. Alternatively or additionally the size of the active area of detector element 18 will limit the field of view to a desired angle by increasing the distance from lens 16 and detector element 18.

In a preferred embodiment of the invention source 10 is a laser diode or LED having a high brightness and a comprising virtually a point source is used and iris 11 may be eliminated. A bright point source allows for substantial reduction of viewing angle and optimal application of the invention.

In a preferred embodiment of the invention, detector element 18 is a photodiode having a very small photosensitive area and iris 20 may not be required.

In a preferred embodiment of the invention the angle of view of detector 18 is limited to less than about ±10 degrees, more preferably to less than about ±5 degrees. As will be seen below, the smaller the angle the greater the selectivity of the system to changes in colored toner concentration as compared to black toner contamination. The only practical limitation on angle is the strength of the source and the sensitivity of the detector.

In an alternative, especially preferred, embodiment of the invention, lenses 12 and 16 are replaced by planar transparent elements, and a collimator is placed after the laser source 10 so as to irradiate only a relatively limited area of the dispersion 14. In this embodiment, the viewing angle is limited as described above, however, the rejection of doubly scattered light is greatly improved. In essence, the requirement that the light come from a small area of the dispersion and arrive at a small angle of incidence, greatly enhances the yellow sensitivity. Preferably, iris 20 is included to further reduce the radiation angle of source 10, thereby further reducing the scattered light received by detector 18.

It has been found by the present inventors that as the viewing angle of detector 18 is reduced, the sensitivity to colored toner, defined as the percent change in signal for a given change in color toner concentration divided by the nominal signal, increases. The sensitivity to black is much less dependent on the viewing angle.

Thus as the angle is decreased, the measurement of the concentration of colored toner becomes much less sensitive to contamination by black particles than for wide fields of view.

In particular, in a typical wide angle system for measuring yellow toner particle concentration, the sensitivity to black contamination is about 50 times that to yellow. Thus, even very small and visually unimportant amounts of black toner contamination, causes large errors in the measurements of yellow concentration. When the angle is limited to about ±5 to ±10 degrees the relative sensitivity is reduced to a factor of about 3 and 10 respectively, depending on the angle of view. For measurements of magenta toner particles the relative sensitivity is reduced from about 30 to about 2–5 depending on the angle.

During calibration one or more dispersions of colored toner particles are tested and the resulting detector output signals are measured. Based on these measurements a sensitivity curve for the system and/or the signal level at which additional toner concentrate should be added to the system is determined. This value and possibly other points on a calibration curve is stored in computing circuitry 24 which may include a computer such as a microprocessor or dedicated analog and/or digital circuitry. In operation in a preferred embodiment of the invention, computing circuitry 24 compares the output of detector 18 with the stored value and when the signal rises above a threshold value, toner concentrate is added to the system.

It will be understood that using the inverse of the preferred embodiment, i.e., having a wide angle detector close to the flow of liquid, the sensitivity to colored particles is reduced and that to black is increased. By placing the detector close to the flow, the sensitivity to black can be made many times as high as that to yellow.

In one embodiment of the invention two measurements are made. In a first step a determination of the black concentration is made as described in the previous paragraph. In a second step a narrow angle measurement is made and a correction to the results is made for black contamination. Such correction will be based on prior measurements of the effects of various levels of black contamination on the narrow angle measurements.

Figure 2:
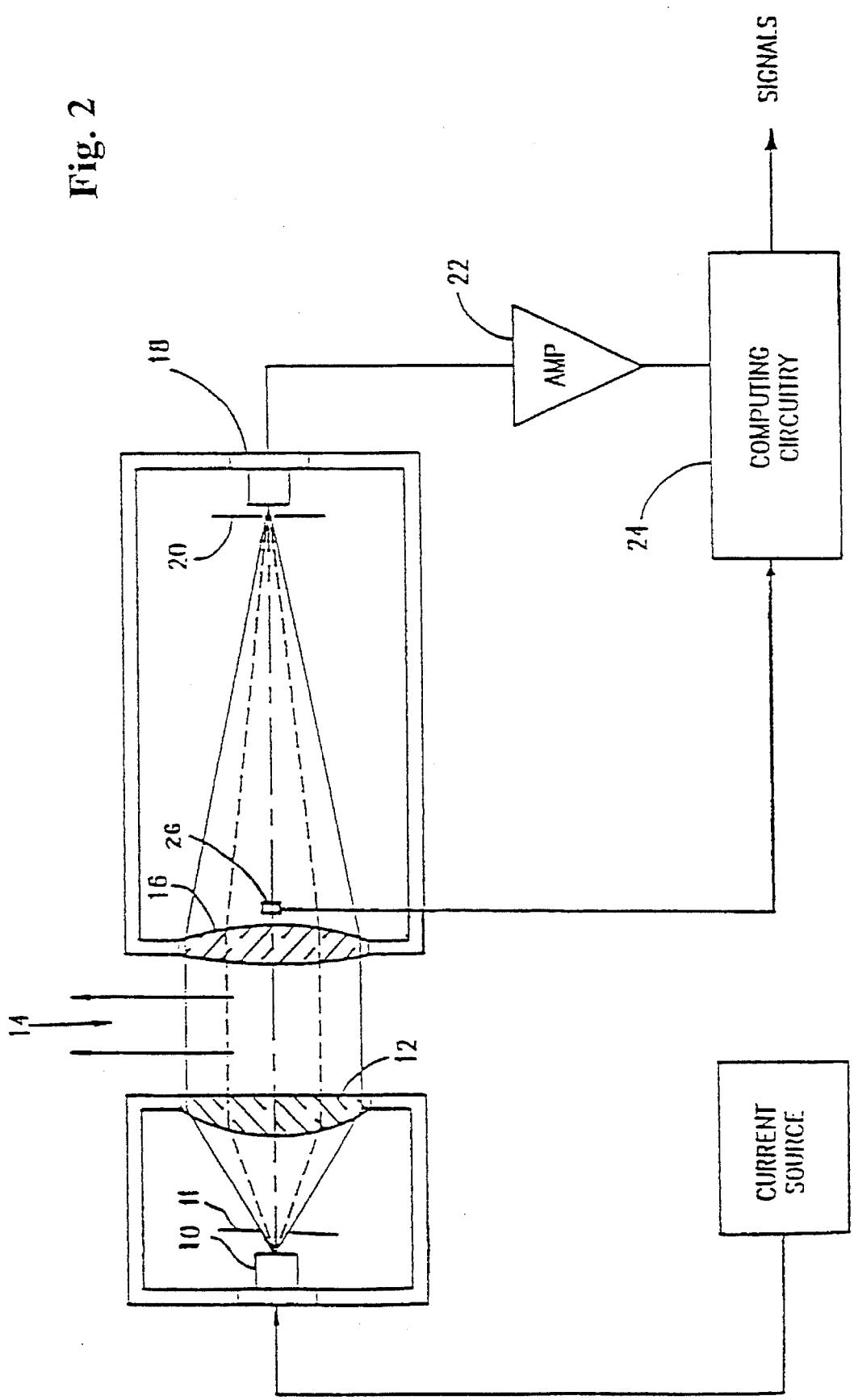
FIG. 2 is a schematic illustration of a concentration detector constructed and operative in accordance with a second embodiment of the present invention.

The wide angle measurement can be made with a separate source of light or in a preferred embodiment of the invention shown in FIG. 2, a second detector 26 viewing the dispersion is placed near lens 16. If this detector is small it will block very little light from detector 18 and have a wide viewing angle of the dispersion. For this configuration, the distance between lenses 12 and 16 should be maximized to reduce the sensitivity to yellow.

It will be appreciated by persons skilled in the art that the present invention is not limited to what has been particularly shown and described hereinabove. Rather the scope of the present invention is defined only by the claims which follow:

We claim:

1. A method for detecting the concentration of colored toner particles in a dispersion undesirably contaminated by black toner particles, the method comprising the steps of:

providing a quantity of the dispersion of colored toner particles optionally contaminated with black toner particles;

illuminating the dispersion;

detecting an amount of light passed through the dispersion with a viewing angle of less than ±10 degrees; and determining the concentration of the colored toner particles utilizing the detected amount of light.

2. A method according to claim 1 and including, as a preparatory step, the step of determining the sensitivities of the detected light to known concentrations of colored toner particles.

3. A method according claim 2 wherein the viewing angle is less than about ±5 degrees.

4. A method according to claim 3 and including the step of correcting for the black toner particle contamination in the dispersion.

5. A method according to claim 4 wherein the method includes the steps of:
 further detecting an amount of light passed through the dispersion with a high viewing angle; and
 determining the concentration of the black toner particles utilizing the detected amount of light.

6. A method according to claim 2 and including the step of correcting for the black toner particle contamination in the dispersion.

7. A method according to claim 6 wherein the method includes the steps of:
 further detecting an amount of light passed through the dispersion with a high viewing angle; and
 determining the concentration of the black toner particles utilizing the detected amount of light.

8. A method according claim 1 wherein the viewing angle is less than about ±5 degrees.

9. A method according to claim 8 and including the step of correcting for the black toner particle contamination in the dispersion.

10. A method according to claim 9 wherein the method includes the steps of:
 further detecting an amount of light passed through the dispersion with a high viewing angle; and
 determining the concentration of the black toner particles utilizing the detected amount of light.

11. A method according to claim 1 and including the step of correcting for the black toner particle contamination in the dispersion.

12. A method according to claim 11 wherein the method includes the steps of:
 further detecting an amount of light passed through the dispersion with a high viewing angle; and
 determining the concentration of the black toner particles utilizing the detected amount of light.

13. Apparatus for detecting concentrations of colored toner particles in the presence of black or other absorbing toner particles comprising:
 a light source;
 a light detector having a field of view of less than about ±10 degrees;
 means for supplying a dispersion of colored toner particles optionally containing undesirable contamination by black toner particles between the light source and the detector; and
 computing circuitry operative for determining the concentration of the colored toner particles utilizing output from the light detector.

14. Apparatus according to claim 13 wherein the light source comprises:
 a laser diode; and
 a collimator.

15. Apparatus according to claim 14 wherein the light detector comprises a focusing lens.

16. Apparatus according to claim 15 wherein the field of view is limited by the size of the detector.

17. Apparatus according to claim 15 wherein the field of view is limited by the size of the lens.

18. Apparatus according to claim 14 wherein the light detector comprises an iris which limits the field of view.

19. Apparatus according to claim 18 wherein the viewing angle is less than about ±5 degrees.

20. Apparatus according to claim 18 and including:
 a second light detector having a large field of view; and
 computing circuitry operative for determining the concentration of the black toner particles utilizing output from the second light detector.

21. Apparatus according to any claim 14 and including means for determining the sensitivities of the detected light to known concentrations of colored toner particles.

22. Apparatus according to claim 21 and including means for determining the concentration of black toner particles contaminating the dispersion.

23. Apparatus according to claim 14 wherein the viewing angle is less than about ±5 degrees.

24. Apparatus according to claim 14 and including means for determining the concentration of black toner particles contaminating the dispersion.

25. Apparatus according to claim 14 and including:
 a second light detector having a large field of view; and
 computing circuitry operative for determining the concentration of the black toner particles utilizing output from the second light detector.

26. Apparatus according to any claim 14 and including means for determining the sensitivities of the detected light to known concentrations of colored toner particles.

27. Apparatus according to claim 13 wherein the light detector comprises a focusing lens.

28. Apparatus according to claim 27 wherein the field of view is limited by the size of the detector.

29. Apparatus according to claim 27 wherein the field of view is limited by the size of the lens.

30. Apparatus according to claim 13 wherein the light detector comprises an iris which limits the field of view.

31. Apparatus according to claim 30 wherein the viewing angle is less than about ±5 degrees.

32. Apparatus according to claim 30 and including:
 a second light detector having a large field of view; and
 computing circuitry operative for determining the concentration of the black toner particles utilizing output from the second light detector.

33. Apparatus according to claim 13 and including means for determining the sensitivities of the detected light to known concentrations of colored toner particles.

34. Apparatus according to claim 33 and including means for determining the concentration of black toner particles contaminating the dispersion.

35. Apparatus according to claim 13 wherein the viewing angle is less than about ±5 degrees.

36. Apparatus according to claim 13 and including means for determining the concentration of black toner particles contaminating the dispersion.

37. Apparatus according to claim 13 and including:
 a second light detector having a large field of view; and
 computing circuitry operative for determining the concentration of the black toner particles utilizing output from the second light detector.

* * * * *